United States Patent
Kim et al.

(10) Patent No.: US 8,877,025 B2
(45) Date of Patent: Nov. 4, 2014

(54) COMBINATORIAL MATERIAL SCREENING METHOD FOR AN ELECTROCHEMICAL CELL

(75) Inventors: Hee Soo Kim, Mountain View, CA (US); John Muldoon, Saline, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 346 days.

(21) Appl. No.: 13/216,327

(22) Filed: Aug. 24, 2011

(65) Prior Publication Data

US 2013/0049759 A1    Feb. 28, 2013

(51) Int. Cl.
- G01N 27/26 (2006.01)
- G01N 27/416 (2006.01)
- H01M 4/38 (2006.01)
- H01M 10/054 (2010.01)
- G01N 27/403 (2006.01)
- H01M 4/58 (2010.01)

(52) U.S. Cl.
CPC ............ H01M 10/054 (2013.01); H01M 4/381 (2013.01); H01M 4/38 (2013.01); H01M 4/5815 (2013.01); Y02E 60/12 (2013.01); G01N 27/403 (2013.01)
USPC ........... 204/412; 204/415; 204/406; 324/437; 324/426; 324/432

(58) Field of Classification Search
USPC ................... 324/432, 437; 204/412, 406, 415
See application file for complete search history.

(56) References Cited

U.S. PATENT DOCUMENTS

| | | | |
|---|---|---|---|
| 3,926,764 A * | 12/1975 | Ruzicka et al. | 204/418 |
| 5,425,870 A | 6/1995 | Stein | |
| 5,686,201 A | 11/1997 | Chu | |
| 6,420,067 B1 | 7/2002 | Yoshioka | |
| 6,733,924 B1 | 5/2004 | Skotheim et al. | |
| 7,029,796 B2 | 4/2006 | Choi et al. | |
| 7,189,477 B2 | 3/2007 | Mikhaylik | |
| 7,316,868 B2 | 1/2008 | Gorkovenko | |

(Continued)

FOREIGN PATENT DOCUMENTS

JP    2004-265675    9/2004

OTHER PUBLICATIONS

Kim et al. (Aug. 2011). Structure and compatibility of a magnesium electrolyte with a sulphur cathode. Nature Communications, 2:427, pp. 1-6, . DOI: 10.1038/ncomms1435.*

(Continued)

*Primary Examiner* — Richard V Muralidar
*Assistant Examiner* — David Henze-Gongola
(74) *Attorney, Agent, or Firm* — Oblon, Spivak, McClelland, Maier & Neustadt, L.L.P.

(57) ABSTRACT

An electrochemical test cell, containing an anode comprising a metal as an active component; a cathode comprising a porous chemically inert tube containing an active material compatible with the metal of the anode; and an electrolyte; wherein the only metal in contact with the electrolyte is the metal of the anode, is provided. This test cell is useful in a method to evaluate various combinations of materials for suitability as a combination for preparation of a battery.

8 Claims, 2 Drawing Sheets

1. Mg reference electrode
2. Working electrode
3. PTFE tube
4. Mg counter electrode
5. Electrolyte
6. S/C paste
7. Potentiostat
8. Porous Tip

(56) References Cited

U.S. PATENT DOCUMENTS

| | | | |
|---|---|---|---|
| 7,361,257 B2 | 4/2008 | Wang et al. | |
| 8,361,661 B2* | 1/2013 | Doe et al. | 429/337 |
| 2008/0182176 A1 | 7/2008 | Aurbach et al. | |
| 2009/0226809 A1 | 9/2009 | Vu et al. | |
| 2010/0004521 A1* | 1/2010 | Epps | 600/347 |
| 2010/0310933 A1* | 12/2010 | Jiang et al. | 429/188 |
| 2012/0312700 A1* | 12/2012 | Bard et al. | 205/794.5 |
| 2013/0065127 A1* | 3/2013 | Nazar et al. | 429/218.1 |
| 2013/0143096 A1* | 6/2013 | Affinito et al. | 429/145 |

OTHER PUBLICATIONS

Aurbach et al. "Progress in Rechargeable Magnesium Battery Technology", Advanced Materials, 19, 4260-4267, 2007.*

Z. Lu, et al. "On the Electrochemical Behavior of Magnesium Electrodes in Polar Aprotic Electrolyte Solutions" Journal of Electroanalytical Chemistry, vol. 466, (pp. 203-217) 1999.

Thomas D. Gregory, et al. "Nonaqueous Electrochemistry of Magnesium" J. Electrochem. Soc., vol. 137, No. 3, (pp. 775-780), 1990.

* cited by examiner

Fig. 1
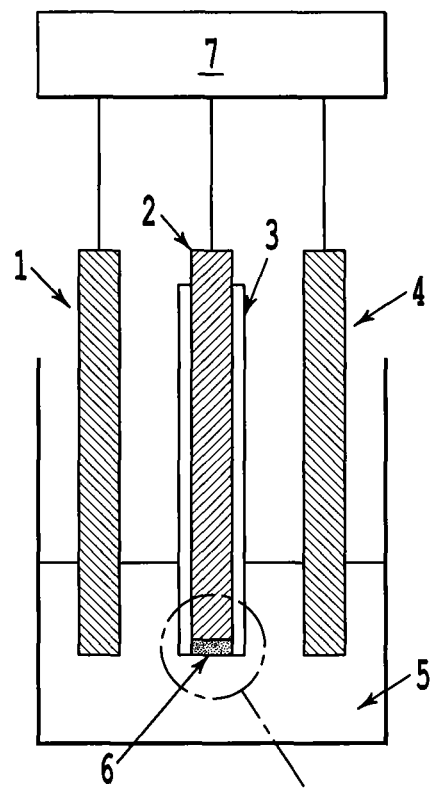
1. Mg reference electrode
2. Working electrode
3. PTFE tube
4. Mg counter electrode
5. Electrolyte
6. S/C paste
7. Potentiostat
8. Porous Tip
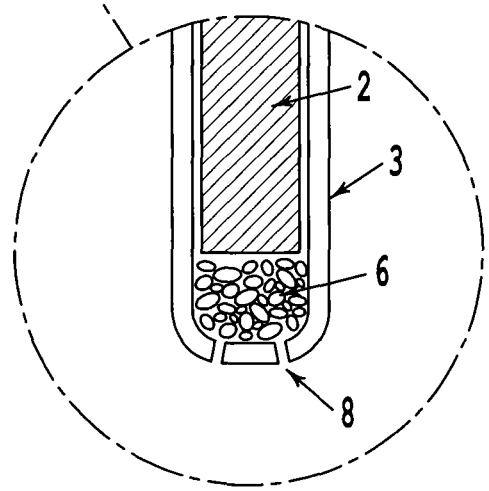
Fig. 1a

COMBINATORIAL MATERIAL SCREENING METHOD FOR AN ELECTROCHEMICAL CELL

BACKGROUND OF THE INVENTION

1. Field of the Invention

The present invention relates to an electrochemical test cell and a method to screen combinations of materials for compatibility and performance in an electrochemical cell.

2. Discussion of the Background

Lithium ion batteries have been in commercial use since 1991 and have been conventionally used as power sources for portable electronic devices. The technology associated with the construction and composition of the lithium ion battery (LIB) has been the subject of investigation and improvement and has matured to an extent where a state of art LIB battery is reported to have up to 700 Wh/L of energy density. However, even the most advanced LIB technology is not considered to be viable as a power source capable to meet the demands for a commercial electric vehicle (EV) in the future. For example, for a 300 mile range EV to have a power train equivalent to current conventional internal combustion engine vehicles, an EV battery pack having an energy density of approximately 2000 Wh/L is required. As this energy density is close to the theoretical limit of a lithium ion active material, technologies which can offer battery systems of higher energy density are under investigation.

Magnesium as a multivalent ion is an attractive alternate electrode material to lithium, which can potentially provide very high volumetric energy density. It has a highly negative standard potential of −2.375V vs. RHE, a low equivalent weight of 12.15 g/eq and a high melting point of 649° C. Compared to lithium, it is easy to handle, machine and dispose. Because of its greater relative abundance, it is lower in cost as a raw material than lithium and magnesium compounds are generally of lower toxicity than lithium compounds. All of these properties coupled with magnesium's reduced sensitivity to air and moisture compared to lithium, combine to make magnesium an attractive alternative to lithium as an anode material.

Production of a battery having an anode based on magnesium, requires a cathode which can reversibly adsorb and desorb magnesium ions and an electrolyte system which will efficiently transport magnesium ions.

The electrochemical behavior of a magnesium electrode in a polar aprotic electrolyte solution was reported by Lu et al. in the Journal of Electroanalytical Chemistry (466 (1999) pp 203-217). These authors concluded that the electrochemical behavior of Mg is different from that of Li in polar aprotic electrolyte solutions. Their investigation showed that in contrast to the case of lithium electrodes, surface films which form on the Mg electrode in the aprotic solvents do not transport Mg ions. Therefore, conventional electrolyte systems are not suitable for a cell having a magnesium anode. Since Mg ion transport is an essential requirement for any electrochemical cell based on a magnesium anode, other electrolyte systems have been investigated.

Gregory et al. (J. Electrochem. Soc., 137 (3), March, 1990, 775-780) reported electrolyte systems of alkylmagnesium halide-organoboron complexes in an ether solvent. Also reported were alkylmagnesium halide solutions to which aluminum halides were added. Mg dissolution and plating at very high current efficiencies, giving bright crystalline Mg deposits were obtained in these systems. However, a suitable cathode material, compatible with the electrolyte system was not reported. The most commonly used magnesium electrolyte to date is an organometallic material such as phenyl magnesium chloride/aluminum chloride in tetrahydrofuran. However, these electrolyte mixtures are not likely to be of practical commercial utility due to air and moisture sensitivity characteristic of such Grignard materials. Moreover, the phenyl magnesium chloride/aluminum chloride electrolyte has limited anodic stability, and significantly, such materials are highly nucleophilic and intrinsically strong reducing agents. This chemical reactivity character is problematic, because to construct an electrochemical cell employing a Grignard type electrolyte, a cathode material which is essentially chemically inert to the Grignard is required.

Sulfur is of low cost and low molecular weight and could be used as a cathodic material in combination with a magnesium anode to provide a high capacity, safe and economic battery, potentially suitable for use in EV. However, the organometallic electrolytes employed in the above magnesium electrolyte systems are highly reactive with sulfur and are known to directly react with sulfur to form sulfides by nucleophilic attack (The Chemistry of the Thiol Group, Pt 1; Wiley, New York, 1974, pp 211-215).

Therefore, in order to produce a Mg/S battery, a new electrolyte system which meets all the requirements for magnesium ion transport described previously while having low or no chemical reactivity toward sulfur is required.

Investigation of such systems is typically complex and problematic in that the ultimate evaluation of suitability and performance is conventionally dependent upon construction of a coin cell which is time consuming and subject to error in construction which may lead to misleading results. Moreover, conventional systems often require utilization of substitute electrodes of a material different from the test material when the test combination is not chemically compatible. This is especially the case in the investigation of potential electrochemical systems wherein the electrolyte is chemically reactive with metal parts, such as a stainless steel current collector used in conventional cells. Therefore, there is a need for a system and method to evaluate various combinations of anode, cathode and electrolyte materials which does not involve the complex fabrication of a coin cell or a system having substitute working electrodes, requires less time than conventionally known methods and provides adequate demonstration of the feasibility and potential electrochemical performance of the test combination as a power source.

The testing methods conventionally known do not meet the described need for a simple, straight forward and accurate test system and method.

For example, U.S. Pre-Grant Publication No. 2010/0310933 to Jiang describes an electrolyte for a cell having a magnesium or magnesium alloy anode and a cathode having an active material which includes iron disulfide. The electrolyte comprises a magnesium salt dissolved in an organic solvent and an additive to retard buildup of a passivation coating on the magnesium anode surface. In preparation of a test cell system, Jiang presses a mixture of iron disulfide and teflonized acetylene black onto an aluminum collector sheet which is therefore in contact with the electrolyte.

U.S. Pre-Grant Publication No. 2009/0226809 to Vu et al. describes a cathode for a lithium-sulfur battery (Abstract). A metal oxide selected from Group I and II metals is included in the composition of a sulfur cathode composition [0012]. The anode contains lithium and the electrolyte described is composed of a lithium salt in a nonaqueous solvent system [0032].

U.S. Pre-Grant Publication No. 2008/0182176 to Aurbach et al. describes an electrochemical cell having a magnesium anode and an intercalation cathode having a modified Chevrel phase. The Chevrel phase compound is represented by the formula $Mo_6S_{8-y}Se_y$ (y is greater than 0 and less than 2) or $M_xMo_6S_8$ (x is greater than 0 and less than 2). This material is coated onto a metal such as aluminum as a current collector. The electrolyte is represented by the formula $Mg(AlR_xCl_{4-x})_2$ and/or $(MgR_2)_x\text{-}(AlCl_{3-n}R_n)_y$ wherein R is methyl, ethyl, butyl, phenyl and derivatives thereof, n is greater than 0 and lower than 3, x is greater than 0 and lower than 3 and y is greater than 1 and lower than (Claim 3) in an ether solvent. Therefore, both magnesium and the metal of the cathode collector are in contact with the electrolyte.

U.S. Pat. No. 7,316,868 to Gorkovenko describes an electrochemical cell having a lithium anode, a cathode of an electroactive sulfur containing composition and a nonaqueous electrolyte containing a lithium salt and a solvent mixture of dioxolane and one or more of 1,2-dialkoxyalkanes of 5 or 6 carbons and 1,3-dialkoxyalkanes of 5 or 6 carbon atoms (Claim 1). Electroactive sulfur compounds include elemental sulfur and organic compounds having sulfur and carbon atoms (Col. 4, lines 10-26). Cathodes were prepared by coating a current collector such a s aluminum with the sulfur containing material. Therefore, both lithium and the metal of the cathode collector are in contact with the electrolyte.

U.S. Pat. No. 7,189,477 to Mikhaylik describes an electrochemical cell having a lithium anode, a cathode of a sulfur containing material and an electrolyte system composed of a lithium salt (Col. 4, lines 5-22) and a non-aqueous oxygen containing organic solvent selected from acyclic ethers, cyclic ethers, polyethers and sulfones. Cathodes were prepared by coating a current collector such a s aluminum with the sulfur containing material. Therefore, both lithium and the metal of the cathode collector are in contact with the electrolyte.

U.S. Pat. No. 7,029,796 to Choi et al. describes lithium sulfur battery having a cathode of an agglomerated complex of sulfur and a conductive agent particles (Claim 1). A solid or liquid electrolyte can be employed and a liquid electrolyte is a nonaqueous organic solvent and a lithium salt (Col. 8, lines 43-58). The agglomerated complex of sulfur is coated on a metal current collector such as stainless steel, aluminum or copper among others. Therefore more than one metal contacts the electrolyte.

U.S. Pat. No. 6,733,924 to Skotheim et al. describes lithium sulfur battery wherein the lithium is protected by a surface coating of a metal such as copper, magnesium, aluminum, silver, etc. (Col. 12, lines 25-28). The electrolyte may be comprised of ionic salts in a non-aqueous solvent, gel polymer or polymer. Ionic electrolyte salts are lithium salts (Col. 15, line 26 to Col. 16, line 27).

U.S. Pat. No. 6,420,067 to Yoshioka describes a hydrogen storage negative electrode being a Mg alloy of Ni, Zn, and Zr (Abstract). The positive electrode is composed of a metal oxide (Col. 3, lines 17-19) and an aqueous electrolyte Col. 7, lines 16-18). Conventional cathodes prepared by coating a metal current collector are employed. Therefore, multiple metals contact the electrolyte.

JP 2004 265675 to Hideyuki et al. describes a nonaqueous electrolyte battery having a magnesium containing anode, a cathode containing sulfur and a reference electrode containing lithium. The reference electrode is apparently necessary because the $Mg(TFSI)_2\text{-}\gamma$-butyrolactone electrolyte employed is not compatible with Mg electrode. Hideyuki does not describe a magnesium sulfur cell where the only metal in contact with the electrolyte is the anode metal.

U.S. Pat. No. 7,361,257 to Wang et al. describes a complex device containing a rotating disk electrode and method to evaluate an electrochemical reaction. The device contains an electrochemical cell containing working electrodes of metals and metal alloys which are stable to high temperatures and does not describe a test system cell where only one metal is in contact with the electrolyte.

U.S. Pat. No. 5,686,201 to Chu describes a positive electrode containing sulfur, an electronic conductor and an ionic conductor. The positive electrode is prepared by depositing a sulfur containing slurry onto a metal current collector. Therefore a test cell wherein only one metal is in contact with the electrolyte is not disclosed or suggested.

U.S. Pat. No. 5,425,870 to Stein describes an instrument for measuring the throwing power, electrochemical efficiency and operating current density of an electrolytic bath for electrolytic processing of materials. Multiple electrodes of different metal construction are contained in the meter.

As indicated, none of these references describing conventional systems discloses or suggests a system and method to evaluate various combinations of anode, cathode and electrolyte materials which does not involve the complex fabrication of a coin cell or a system having substitute working electrodes, and provides adequate demonstration of the feasibility and potential electrochemical performance of the test combination as a power source.

SUMMARY OF THE INVENTION

This and other objects, individually or in combinations thereof, have been achieved by the present invention, a first embodiment of which includes an electrochemical test cell, comprising:

an anode comprising a metal as an active component;

a cathode comprising a porous chemically inert tube containing an active material compatible with the metal of the anode; and an electrolyte;

wherein the only metal in contact with the electrolyte is the metal of the anode.

A second embodiment of the present invention provides an electrochemical test cell according to the first embodiment wherein the metal active component of the anode is selected from alkali metals and alkaline earth metals the only metal in contact with the electrolyte is the alkali metal or the alkaline earth metal of the anode.

A third embodiment of the present invention provides an electrochemical test cell according to the first embodiment wherein the metal active component of the anode is magnesium and the only metal in contact with the electrolyte is magnesium.

A fourth embodiment of the present invention provides an electrochemical test cell according to the first embodiment, wherein the cathode active material comprises sulfur wherein the only metal in contact with the electrolyte is the metal of the anode.

A fifth embodiment of the present invention provides an electrochemical test cell wherein the metal active component of the anode is magnesium and the cathode active material comprises sulfur wherein the only metal in contact with the electrolyte is magnesium.

A sixth embodiment of the present invention provides a method for screening a combination of anode, cathode and electrolyte components for suitability and performance in an electrochemical cell, comprising:

charging the electrochemical test cell according to the first embodiment with a combination of an anode metal, cathode active material and an electrolyte:

and measuring an electrochemical performance of the charged cell.

A seventh embodiment of the present invention provides a method for screening an electrolyte for suitability and performance in an electrochemical cell, having an anode comprising magnesium as an active ingredient and a cathode comprising sulfur as an active ingredient, comprising:

constructing the electrochemical test cell according to the first embodiment with an anode comprising magnesium metal as the active material and with a cathode comprising sulfur as active material and an electrolyte:

adding an electrolyte to be screened;

and measuring an electrochemical performance of the charged cell.

BRIEF DESCRIPTION OF THE DRAWINGS

FIG. 1 shows an electrochemical test cell according to the invention.

DETAILED DESCRIPTION OF THE INVENTION

Figure 2:
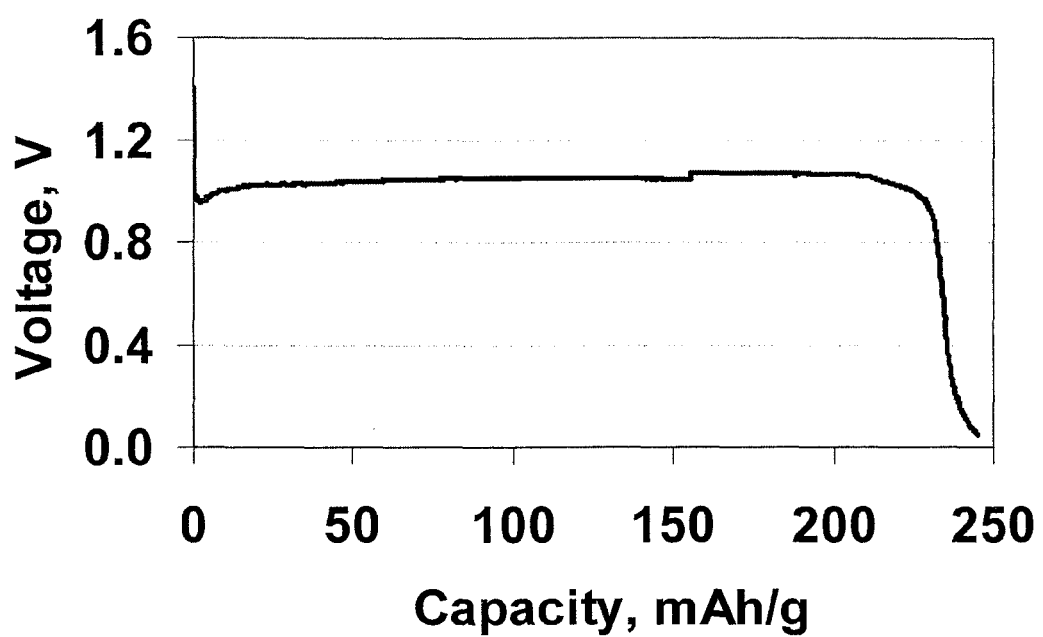
FIG. 2 shows the discharge performance of a test cell according to an embodiment of the invention.

It is an object of the present invention to provide an electrochemical test cell to evaluate various combinations of anode, cathode and electrolyte materials which does not involve the complex fabrication of a coin cell or a system having substitute working electrodes, and provides adequate demonstration of the feasibility and potential electrochemical performance of the test combination as a power source.

A second object of the present invention is to provide an electrochemical test cell to evaluate various combinations of cathode active materials and electrolyte materials with an anode containing an alkali metal or an alkaline earth metal as the active material and to provides adequate demonstration of the feasibility and potential electrochemical performance of the test combination as a power source.

A third object of the present invention is to provide an electrochemical test cell to evaluate various combinations of cathode active materials and electrolyte materials with an anode containing magnesium metal as the active material and to provides adequate demonstration of the feasibility and potential electrochemical performance of the test combination as a power source.

A fourth object of the present invention is to provide an electrochemical test cell having an anode containing magnesium as the active material, a cathode containing sulfur as the active material and a nonaqueous electrolyte system and to provides adequate demonstration of the feasibility and potential electrochemical performance of the test combination as a power source.

These and other objects, individually or in combinations thereof, have been achieved by the present invention, a first embodiment of which includes an electrochemical test cell, comprising:

an anode comprising a metal as an active component;

a cathode comprising a porous chemically inert tube containing an active material compatible with the metal of the anode; and an electrolyte;

wherein the only metal in contact with the electrolyte is the metal of the anode.

A second embodiment of the present invention provides an electrochemical test cell according to the first embodiment wherein the metal active component of the anode is selected from alkali metals and alkaline earth metals the only metal in contact with the electrolyte is the alkali metal or the alkaline earth metal of the anode.

A third embodiment of the present invention provides an electrochemical test cell according to the first embodiment wherein the metal active component of the anode is magnesium and the only metal in contact with the electrolyte is magnesium.

A fourth embodiment of the present invention provides an electrochemical test cell according to the first embodiment, wherein the cathode active material comprises sulfur wherein the only metal in contact with the electrolyte is the metal of the anode.

A fifth embodiment of the present invention provides an electrochemical test cell wherein the metal active component of the anode is magnesium and the cathode active material comprises sulfur wherein the only metal in contact with the electrolyte is magnesium.

A sixth embodiment of the present invention provides a method for screening a combination of anode, cathode and electrolyte components for suitability and performance in an electrochemical cell, comprising:

charging the electrochemical test cell according to the first embodiment with a combination of an anode metal, cathode active material and an electrolyte:

and measuring an electrochemical performance of the charged cell.

A seventh embodiment of the present invention provides a method for screening an electrolyte for suitability and performance in an electrochemical cell, having an anode comprising magnesium as an active ingredient and a cathode comprising sulfur as an active ingredient, comprising:

constructing the electrochemical test cell according to the first embodiment with an anode comprising magnesium metal as the active material and with a cathode comprising sulfur as active material and an electrolyte:

adding an electrolyte to be screened;

and measuring an electrochemical performance of the charged cell.

In the study of potential new electrochemical systems for the purpose of developing new batteries which may meet the demands for a commercial electric vehicle (EV) in the future, the inventors have surprisingly discovered a simple and efficient method to test combinations of anode, cathode and electrolyte active materials, which avoids interaction of the electrolyte system with any metal other than the anode metal.

The inventors have learned that a working cathode can be constructed from an appropriately shaped tube of material, chemically inert to the electrolyte system which contains an opening or porosity in the tip of the tube. A material to be tested for cathodic performance with a particular combination of anode and electrolyte can be placed in the tip as a paste, either undiluted or diluted with another conventionally known cathodic material such as finely divided carbon. According to the invention, only the material placed in the tip contacts the electrolyte and the electroconductive working electrode (2) as shown in FIG. 1 is not in contact with the electrolyte. A reference electrode and counter electrode may then be constructed of the same material. In this manner the only metal in contact with the electrolyte is the anode metal. FIG. 1 shows the components and the schematic arrangement of the components of the test cell according to the invention.

According to FIG. 1, the electrochemical test cell contains a Mg reference electrode (1) and a Mg counter electrode (anode) (4). The working electrode (2) is located within the PTFE tube (3). The porous tip (8) of the PTFE tube (3), between the porous tip and the bottom end of the working electrode contains the sulfur/carbon (S/C) paste (6). The porosity of the tip (8) allows the S/C paste to interact with the electrolyte (5), but prevents contact of the working electrode (2) with the electrolyte (5).

The metal active component of the anode may be selected from alkali metals and alkaline earth metals or any other material which may serve in an anode capacity.

For example, in the study of potential systems for utility of a Mg/S battery, the reference and counter electrode may be constructed from magnesium metal and the tip of the working cathode filled with a sulfur paste or a paste of sulfur with another material such as finely divided carbon. FIG. 1 specifically shows this embodiment of the invention. The utility of test electrolyte systems may then be evaluated by completing construction of the cell by addition of the electrolyte system and measuring, for example, the discharge behavior of the test cell. In this embodiment, the tip of the cathode tube is filled with a sulfur/carbon paste. A binder which is inert to the electrolyte may optionally be contained in the paste to give stability and structure to the paste. Polytetrafluoroethylene may be employed as a binder.

In a preferred embodiment of the invention, the sulfur/carbon paste may contain 45 to 75 weight % sulfur relative to the total weight of the paste. This range includes all values and subvalues therebetween, preferably including 50 to 70 weight % sulfur and most preferably 55 to 65 weight % sulfur. The optional binder may be present in an amount of 1 to 10 weight % relative to the total weight of the paste. This range includes all values and subvalues therebetween, preferably including 2 to 8 weight % and most preferably 3 to 6 weight % relative to the total weight of the paste.

As would be obvious to one of ordinary skill in the art, the test cell of the invention is not limited to testing of electrolyte systems, but may be applied to evaluation of anodic and cathodic materials equally, as well. In one embodiment of the present invention, a method for screening a series of materials for electrochemical performance would involve selecting and fixing the material for any two of anode, cathode and electrolyte materials and varying and evaluating the material of the third component of the potential cell.

The hollow tube employed to prepare a non-metal electrode, for example a sulfur cathode as shown in FIG. 1, may be constructed of any material which is chemically inert to the electrolyte and is electrically nonconductive. Polytetrafluoroethylene (PTFE) may be a preferred material for this purpose.

The working electrode portion (2) of the cathode of may be any material which is electroconductive. In a preferred embodiment, the working electrode portion may be a brass rod which is encapsulated in the PTFE tube.

The electrochemical performance of the cell may be appropriately measured by a Potentiostat (7) attached to each of the electrodes.

Having generally described this invention, a further understanding can be obtained by reference to certain specific examples which are provided herein for purposes of illustration only and are not intended to be limiting unless otherwise specified.

EXAMPLES

Example 1

An electrochemical test cell was constructed as shown schematically in FIG. 1. The reference electrode and the counter electrode were made from magnesium metal. The working electrode of the three electrode cell was made by filling the tip of a PFTE tube with a paste comprising 60% elemental sulfur, 36% finely divided carbon and 4% polytetrafluoroethylene.

All reagents were purchased from Synthonix. In a drybox, 15 ml of 0.5 M solution o aluminum trichloride solution was treated with 2 eq of 1.44 M THF solution of hexamethyldisilazide (HMDS)MgCl (10.417 mL, 15 mmol). The flask was capped and stirred rapidly for 48 hrs. The solution was transferred to 125 mL conical flask, and the THF solution was layered with dry hexane (Aldrich, 80 mL). After 3 days, the white crystals were filtered and washed with hexane (30 mL) and vacuum dried to furnish 4.3 g of $(Mg_2Cl_3\text{-}6THF)^+ [AlCl_3(HMDS)]^-$.

The white crystal was dissolved in THF to make 0.2M solution, and was used as the electrolyte in the 3-electrode test cell shown in FIG. 1. Using this cell, the electrochemical performance of an electrochemical cell having a magnesium anode, sulfur cathode and $(Mg_2Cl_3\text{-}6THF)^+ [AlCl_3(HMDS)]^-$ as electrolyte was demonstrated. The discharge behavior of the cell is shown in FIG. 2.

The invention claimed is:

1. An electrochemical test cell, comprising:
   an anode comprising a metal as an active component;
   a reference electrode comprising the same metal as the anode;
   an electrolyte; and
   a cathode;
   the cathode comprising: a hollow tube with a closed tip; an active material comprising elemental sulfur compatible with the metal of the anode within the tube at the tip; and a working electrode above the tip in contact with the active material and not in contact with the electrolyte;
   wherein
   at least the tip of the cathode is in contact with the electrolyte,
   the tube of the cathode consists of a material which is chemically inert to the electrolyte and is electrically nonconductive,
   the closed tip of the cathode is porous or the tip comprises an opening, and
   the only metal in contact with the electrolyte is the metal of the anode and the reference electrode.

2. The electrochemical test cell according to claim 1, wherein the metal active component of the anode and reference electrode is selected from alkali metals and alkaline earth metals.

3. The electrochemical test cell according to claim 2, wherein the metal active component of the anode and reference electrode is magnesium.

4. A method for screening a combination of anode, cathode and electrolyte components for suitability and performance in an electrochemical cell, comprising:
   charging the electrochemical test cell according to claim 1, with a combination of an anode metal, reference electrode, cathode active material and an electrolyte:
   and measuring an electrochemical performance of the charged cell.

5. The method according to claim 4, wherein the active metal charged to the anode and reference electrode is an alkali metal, an alkaline earth metal or a combination thereof.

6. The method according to claim 5, wherein the active metal charged to the anode and reference electrode comprises magnesium.

7. The method according to claim 4, wherein the active metal charged to the anode and reference electrode comprises magnesium, the cathode active material comprises sulfur, and a test electrolyte is screened for electrochemical performance.

8. A method for screening a series of materials for electrochemical performance, comprising:

selecting and fixing the material for any two of an anode and reference electrode metal, a cathode and an electrolyte material;

constructing a test cell of the two selected and fixed materials; and varying and evaluating an electrochemical performance of the cell containing material of the third component not selected and fixed;

wherein the test cell comprises:

a metal counter electrode, a metal reference electrode;

a cathode working electrode comprising:

a hollow tube with a closed tip;

a cathode active material comprising elemental sulfur within the tube at the tip and a working electrode above the tip in contact with the active material;

an electrolyte; and a potentiostat electrically connected to the metal counter electrode, metal reference electrode and cathode working electrode;

wherein at least the tip of the cathode is in contact with the electrolyte, the tube of the cathode consists of a material which is chemically inert to the electrolyte and is electrically nonconductive, the tip of the cathode is porous or the tip comprises an opening, and the metal of the metal counter electrode and metal reference electrode is the same and is the only metal in contact with the electrolyte in the test cell.

* * * * *